(12) United States Patent
Kim (10) Patent No.: US 11,452,928 B2
(45) Date of Patent: Sep. 27, 2022

(54) SYSTEM FOR PROVIDING VIRTUAL EXERCISING PLACE

(71) Applicant: Jae Hwan Kim, Jeollanam-do (KR)

(72) Inventor: Jae Hwan Kim, Jeollanam-do (KR)

( * ) Notice: Subject to any disclaimer, the term of this patent is extended or adjusted under 35 U.S.C. 154(b) by 269 days.

(21) Appl. No.: 16/914,925

(22) Filed: Jun. 29, 2020

(65) Prior Publication Data

US 2021/0001205 A1     Jan. 7, 2021

Related U.S. Application Data

(60) Provisional application No. 62/869,794, filed on Jul. 2, 2019.

(51) Int. Cl.
*A63B 71/06*        (2006.01)
*H04N 7/18*        (2006.01)
(Continued)

(52) U.S. Cl.
CPC ...... *A63B 71/0622* (2013.01); *A63B 24/0062* (2013.01); *G06F 3/017* (2013.01);
(Continued)

(58) Field of Classification Search
CPC ............ A63B 71/0622; A63B 24/0062; A63B 2024/0093; A63B 2071/0638;
(Continued)

(56) References Cited

U.S. PATENT DOCUMENTS 13,712 A    10/1855   Yard
43,325 A    6/1864    Merrill
(Continued)

FOREIGN PATENT DOCUMENTS

KR    1020040088184 A    10/2004
KR    1020050021032 A     3/2005
(Continued)

OTHER PUBLICATIONS

Grant of Patent dated Mar. 27, 2018, 2 pages, issued in Korean Patent Application No. 10-2017-0152555.
(Continued)

*Primary Examiner* — Sundhara M Ganesan
(74) *Attorney, Agent, or Firm* — Avek IP, LLC (57) ABSTRACT

The disclosed technology relates to a system for providing virtual exercise place, which displays a user-selected virtual exercise place, and shares the display of the selected virtual exercise place with other users in real time or at a different time in order to exercise together. The system comprises an image information database in which location-based image data related to a virtual exercise place is stored; and an image data controller which selects from the image information database the location-based image data related to the virtual exercise place received from a terminal, transmits them to the terminal, displays on the terminal the exercise place image data corresponding to an exercise start location received from the terminal, receives an exercise distance information calculated by fitness equipment, and displays on the terminal the exercise place image data corresponding to a location moved by the exercise distance from the exercise start location.

6 Claims, 9 Drawing Sheets

(51) Int. Cl.
  *G06F 3/01*    (2006.01)
  *G16H 20/30*   (2018.01)
  *G06F 16/54*   (2019.01)
  *G06F 16/587*  (2019.01)
  *A63B 24/00*   (2006.01)
  *G06F 3/14*    (2006.01)

(52) U.S. Cl.
  CPC ............ *G06F 3/1454* (2013.01); *G06F 16/54* (2019.01); *G06F 16/587* (2019.01); *G16H 20/30* (2018.01); *H04N 7/18* (2013.01); *A63B 2024/0093* (2013.01); *A63B 2071/0638* (2013.01); *A63B 2071/0675* (2013.01); *A63B 2220/05* (2013.01); *A63B 2220/20* (2013.01); *A63B 2220/806* (2013.01); *A63B 2220/808* (2013.01)

(58) Field of Classification Search
  CPC ........ A63B 2071/0675; A63B 2220/05; A63B 2220/20; A63B 2220/806; A63B 2220/808; G06F 3/017; G06F 3/1454; G06F 16/54; G06F 16/587; G06F 3/011; G06F 2203/012; G16H 20/30; H04N 7/18; H04N 7/147
  See application file for complete search history.

(56) References Cited

U.S. PATENT DOCUMENTS

| | | | |
|---|---|---|---|
| 88,184 A | 3/1869 | Lafferty | |
| 117,104 A | 7/1871 | Northup | |
| 152,555 A | 6/1874 | Gorton | |
| 1,675,331 A | 7/1928 | Day | |
| 1,780,743 A | 11/1930 | Codwise | |
| 1,803,507 A * | 5/1931 | O'Neill | B64F 1/36 244/114 R |
| 1,831,730 A | 11/1931 | Fredrik | |
| 3,103,517 A | 9/1963 | Prosser | |
| 6,152,856 A * | 11/2000 | Studor | A63F 13/65 482/4 |
| 7,497,812 B2 | 3/2009 | Neff et al. | |
| 7,549,947 B2 * | 6/2009 | Hickman | G16H 20/30 482/4 |
| 7,833,135 B2 | 11/2010 | Radow et al. | |
| 8,021,270 B2 | 9/2011 | D'Eredita | |
| 8,103,517 B2 | 1/2012 | Hinnebusch | |
| 9,661,355 B2 * | 5/2017 | Ho | H04N 21/23614 |
| 10,117,602 B1 * | 11/2018 | Berme | A61B 5/1128 |
| 10,540,483 B2 * | 1/2020 | Hardee | G16H 50/70 |
| 10,610,725 B2 | 4/2020 | Schaefer et al. | |
| 11,179,617 B2 * | 11/2021 | Chen | A63B 24/0062 |
| 11,191,996 B2 * | 12/2021 | Fung | A63B 22/0292 |
| 11,331,557 B2 * | 5/2022 | Summit | A63B 69/0048 |
| 2002/0045519 A1 * | 4/2002 | Watterson | A63B 22/0023 482/54 |
| 2002/0055419 A1 * | 5/2002 | Hinnebusch | A63B 24/0084 482/8 |
| 2004/0088184 A1 | 5/2004 | Nijdam et al. | |
| 2004/0127272 A1 * | 7/2004 | Park | A63F 13/35 463/6 |
| 2006/0040793 A1 * | 2/2006 | Martens | G16H 20/30 482/8 |
| 2007/0043325 A1 | 2/2007 | Guala | |
| 2007/0093360 A1 * | 4/2007 | Neff | A63B 22/0605 482/8 |
| 2009/0011907 A1 * | 1/2009 | Radow | B62M 3/00 482/57 |
| 2009/0023553 A1 | 1/2009 | Shim | |
| 2009/0023554 A1 * | 1/2009 | Shim | A63B 22/02 482/4 |
| 2010/0004097 A1 * | 1/2010 | D'Eredita | A63B 71/0622 482/8 |
| 2010/0035726 A1 * | 2/2010 | Fisher | A63B 24/0084 482/8 |
| 2012/0117104 A1 | 5/2012 | Stundner et al. | |
| 2014/0046677 A1 * | 2/2014 | Bar-Or | G16H 20/60 705/2 |
| 2014/0244008 A1 * | 8/2014 | Kennett | A63F 13/798 700/91 |
| 2015/0302766 A1 * | 10/2015 | Oberlander | G06Q 10/10 434/247 |
| 2016/0250519 A1 * | 9/2016 | Watterson | A63B 24/0084 482/4 |
| 2016/0300390 A1 * | 10/2016 | Malafeew | G16H 20/30 |
| 2017/0152555 A1 * | 6/2017 | Inoue | C12N 15/09 |
| 2017/0216667 A1 * | 8/2017 | Garvey | A61B 5/681 |
| 2017/0309198 A1 * | 10/2017 | Johnson | G06V 20/46 |
| 2018/0013712 A1 * | 1/2018 | Yin | H04L 67/306 |
| 2018/0099178 A1 * | 4/2018 | Schaefer | A63B 24/0075 |
| 2018/0174347 A1 * | 6/2018 | Chaney | G09G 5/377 |
| 2018/0227706 A1 * | 8/2018 | Cho | G16H 20/30 |
| 2019/0209891 A1 * | 7/2019 | Fung | G06F 3/0338 |
| 2019/0259292 A1 * | 8/2019 | Williams | G09B 5/06 |
| 2020/0139194 A1 * | 5/2020 | Min | A63F 13/847 |
| 2020/0297269 A1 * | 9/2020 | Vieri | A61B 5/6806 |
| 2020/0376339 A1 * | 12/2020 | Chu | A63B 21/00058 |
| 2021/0335145 A1 * | 10/2021 | Denn | G02B 27/017 |
| 2021/0379469 A1 * | 12/2021 | Mann | A63B 22/02 |
| 2021/0404826 A1 * | 12/2021 | Yu | G06T 19/006 |
| 2022/0080284 A1 * | 3/2022 | Churchman | A63B 24/0087 |
| 2022/0156653 A1 * | 5/2022 | Abelow | G06Q 40/12 |

FOREIGN PATENT DOCUMENTS

| | | |
|---|---|---|
| KR | 1020070043325 A | 4/2007 |
| KR | 1020070115210 A | 12/2007 |
| KR | 100853993 B1 | 8/2008 |
| KR | 1020090129077 A | 12/2009 |
| KR | 1020100113945 A | 10/2010 |
| KR | 1020120117104 A | 10/2012 |
| KR | 101461202 B1 | 11/2014 |
| KR | 101675331 B1 | 11/2016 |
| KR | 101780743 B1 | 9/2017 |
| KR | 101803507 B1 | 11/2017 |
| KR | 1020170009376 B1 | 11/2017 |
| KR | 101831730 B1 | 2/2018 |
| KR | 20180013712 A | 2/2018 |
| KR | 101874262 B1 | 7/2018 |
| WO | 2016132844 A1 | 8/2016 |

OTHER PUBLICATIONS

Office Action dated Dec. 12, 2017, 12 pages, issued in Korean Patent Application No. 10-2017-0152555.

Notice of Allowance, dated Jun. 10, 2021, 9 pages, issued in U.S. Appl. No. 16/572,209.

* cited by examiner

SYSTEM FOR PROVIDING VIRTUAL EXERCISING PLACE

CROSS REFERENCE TO RELATED APPLICATIONS

The application claims priority to U.S. Provisional Patent Application 62/869,794 filed on Jul. 2, 2019 and titled "SYSTEM FOR PROVIDING VIRTUAL EXERCISING PLACE," the disclosure of which is incorporated by reference herein in its entirety.

FIELD OF THE DISCLOSURE

The disclosure relates generally to systems and methods for providing virtual exercise places. Some implementations of the disclosed technology relate to a system for providing a virtual exercise place, wherein the virtual exercise place selected by a user is displayed on a terminal and the user can exercise while sharing the image of the selected virtual exercise place with other users in real time or at a different time.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere herein.

Various implementations are provided to introduce a unique manner of providing a virtual exercise place, wherein a virtual exercise place selected by a user is displayed on a screen disposed around fitness equipment and the user can take exercise along with other users while sharing the display of the selected virtual exercise place with them in real time or at a different time so that the user can take exercise while virtually moving within the selected virtual exercise place.

Some implementations of the disclosed technology provide a system for providing virtual exercise place. The system may include a terminal and a fitness equipment capable of calculating an exercise distance. The fitness equipment transmits an image of a virtual exercise place to the terminal and may include an image information database in which location-based image data related to a virtual exercise place is stored; and an image data controller selecting from the image information database the location-based image data related to the virtual exercise place (hereinafter "location-based image data related to the virtual exercise place" is referred to as "exercise place image data") received from the terminal, transmits them to the terminal, displays on the terminal the exercise place image data corresponding to an exercise start location received from the terminal, receives exercise distance information calculated by the fitness equipment, and displays on the terminal the exercise place image data corresponding to a location moved by the exercise distance from an exercise start location (hereinafter "the location moved by an exercise distance from an exercise start location" is referred to as "virtual current location").

In one aspect, when the virtual current location reaches a course selection point of the exercise place image data, the image data controller may transmit a course selection message to the terminal, and display on the terminal the exercise place image data corresponding to the course selected from the terminal.

In another aspect, the image information database may include gradient data of each location of the location-based image data related to the virtual exercise place, wherein the system for providing virtual exercise place may be connected to a load control device of the fitness equipment, and further include a slope activation unit that applies load based on gradient data corresponding to the virtual current location to the fitness equipment.

Some implementations of the disclosed technology provide a system for providing virtual exercise place, which is connected to terminals and fitness equipment capable of calculating an exercise distance and transmits an image of a virtual exercise place to the terminals. The system may include an image information database in which location-based image data related to the virtual exercise place is stored; and a participant setting unit which transmits a signal for asking an exercise participation intention received from a first terminal to a second terminal, and receives a joint exercise start signal to accept an exercise participation from the second terminal; the image data controller which selects from the image information database the location-based image data related to the virtual exercise place received from the first terminal, transmits them to the first terminal and the second terminal, displays on the first terminal and the second terminal the exercise place image data corresponding to the exercise start location received from the first terminal or the second terminal, receives the exercise distance information calculated by the first fitness equipment and a second fitness equipment, and displays on the first terminal and the second terminal the exercise place image data corresponding to a location moved by the exercise distance from the exercise start location (hereinafter "location moved by the exercise distance from the exercise start location" is referred to as "virtual current location").

In one aspect, when the virtual current location reaches a course selection point in the exercise place image data, the image data controller may transmit a course selection message to the first terminal and the second terminal, and display on the first terminal and the second terminal the exercise place image data corresponding to the course first selected by any one of the first terminal and the second terminal.

In another aspect, the first terminal and the second terminal may include a camera and a microphone, wherein the system for providing virtual exercise place may further include a video chatting controller which receives from the first terminal and the second terminal the video data of the first user using the first terminal and the second user using the second terminal, photographed by the cameras of the first terminal and the second terminal, and the audio data including the voice of the first user and the second user, recorded by the microphone of the first terminal and the second terminal, transmits the video data and the audio data of the first user to the second terminal, and transmits the video data and the audio data of the second user to the first terminal.

In another aspect, the image information database may include gradient data for each location of the location-based image data related to the virtual exercise place, wherein the system for providing virtual exercise place may be connected to a load control device of the first fitness equipment and the second fitness equipment, and further include a slope activation unit that applies load based on the gradient data corresponding to the virtual current location to the first fitness equipment and the second fitness equipment.

Some implementations of the disclosed technology provide a system for providing virtual exercise place, which is connected to the terminals including a camera and a microphone and the fitness equipment capable of calculating an exercise distance and transmits an image of the virtual exercise place to the terminals, may include an image information database in which location-based image data related to the virtual exercise place is stored; the participant setting unit which transmits a signal for asking an exercise participation intention received from a first terminal to a second terminal, and receives a joint exercise start signal to accept an exercise participation from the second terminal; the image data controller which selects from the image information database the location-based image data related to the virtual exercise place (hereinafter "location-based image data related to a virtual exercise place" is referred to as "exercise place image data") received from the first terminal, transmits them to the first terminal and the second terminal, displays on the first terminal and the second terminal the exercise place image data corresponding to the exercise start location received from the first terminal or the second terminal, receives the exercise distance information calculated by the first fitness equipment and the second fitness equipment, and displays on the first terminal and the second terminal the exercise place image data corresponding to the location moved by the exercise distance from the exercise start location (hereinafter "location moved by an exercise distance from an exercise start location" is referred to as "virtual current location"); and a video chatting controller which receives from the first terminal and the second terminal the video data of the first user using the first terminal and the second user using the second terminal, photographed by the cameras of the first terminal and the second terminal, and the audio data including the voice of the first user and the second user, recorded by the microphones of the first terminal and the second terminal, transmits the video data and the audio data of the first user to the second terminal, and transmits the video data and the audio data of the second user to the first terminal, wherein when the virtual current location of a third terminal, which the first terminal did not ask an exercise participation intention, approaches the virtual current location of the first terminal or the second terminal, the video chatting controller may receive from the third terminal the video data of a third user using the third terminal, photographed by the camera of the third terminal, and the audio data including the voice of the third user, recorded by the microphone of the third terminal, transmit the video data and the audio data of the third user to the first terminal and the second terminal, and transmit the video data and the audio data of the first user and the second user to the third terminal, and wherein when the third terminal transmits a joint signal to the first terminal or the second terminal through the participant setting unit, the image data controller may display on the third terminal the exercise place image data corresponding to the virtual current location of the first terminal and the second terminal.

Some implementations of the disclosed technology provide a system for providing virtual exercise place, which is connected to a terminal and fitness equipment capable of calculating an exercise distance and transmits an image of a virtual exercise place to the terminal, may include an image information database in which location-based image data related to the virtual exercise place is stored; an image data controller which selects from the image information database the location-based image data related to the virtual exercise place (hereinafter "location-based image data related to the virtual exercise place" is referred to as "exercise place image data") received from a first terminal, transmits them to the first terminal, displays on the first terminal the exercise place image data corresponding to an exercise start location received from the first terminal, receives the exercise distance information calculated by a first fitness equipment, and displays on the first terminal the exercise place image data corresponding to a location moved by an exercise distance from an exercise start location (hereinafter "location moved by an exercise distance from an exercise start location" is referred to as "virtual current location"); and an exercise record database which stores the exercise place image data displayed on the first terminal that is from the exercise start location to the virtual current location (hereafter, "exercise place image data displayed on the first terminal that is from the exercise start location to the virtual current location" is referred to as "first exercise place image data"), wherein when a joint exercise start signal is transmitted from a second terminal, the image data controller displays the stored first exercise place image data on the second terminal.

In one aspect, the image data controller may receive the exercise distance information calculated by a second fitness equipment, and display the stored first exercise place image data corresponding to the virtual current location of the second fitness equipment.

In another aspect, the system for providing virtual exercise place may further include a fitness equipment controller which controls a speed of the second fitness equipment, wherein the fitness equipment controller may change the speed of the second fitness equipment in accordance with the speed at which the virtual current location of the first exercise place image data changes. The first terminal may include a camera and a microphone, wherein the first exercise place image data may include the video data of the first user using the first fitness equipment, photographed by the camera of the first terminal, and the audio data including the voice of the first user, recorded by the microphone of the first terminal.

In another aspect, the second terminal may include a camera and a microphone, wherein the system for providing virtual exercise place may further include an exercise result transmitting unit which with the first exercise place imaged data displays the video data of the second user using the second fitness equipment, photographed by the camera of the second terminal, and transmits image data displayed on the second terminal to a member account of the first user.

In another aspect, the second terminal and a third terminal may include a camera and a microphone, wherein the system for providing virtual exercise place may further include a video chatting controller which receives from the second terminal and the third terminal the video data of the second user using the second terminal and the third user using the third terminal, photographed by the cameras of the second terminal and the third terminal, and the audio data including the voice of the second user and third user, recorded by the microphones of the second terminal and the third terminal, transmits the video data and the audio data of the second user to the third terminal, and transmits the video data and the audio data of the third user to the second terminal, wherein when the virtual current location of the third terminal approaches the virtual current location of the second terminal, the video chatting controller receives from the third terminal the video data of the third user, photographed by the camera of the third terminal, and the audio data including the voice of the third user, recorded by the microphone of the third terminal, and transmits the video data and the audio data of the third user to the second terminal, wherein the system for providing virtual exercise place may further include a participant setting unit which transmits to the third terminal a signal for asking an exercise participation intention received from the second terminal, and receives a joint exercise start signal to accept an exercise participation from the third terminal, and wherein when the third terminal transmits the joint exercise start signal to the second terminal through the participant setting unit, the image data controller may display on the third terminal the first exercise place image data corresponding to the virtual current location of the second terminal.

BRIEF DESCRIPTION OF THE SEVERAL VIEWS OF THE DRAWINGS

A brief description of each drawing is provided so that the drawings cited in this specification are understood more fully.

DETAILED DESCRIPTION

The importance of exercise cannot be emphasized enough. However, an exercise is hard to continue in a long period of time because it is boring and difficult. Exercise alone, for instance, walking, running, or cycling, is a sort of exercise that achieves target amount alone without a partner, and demands strong will to continue exercise in a long term. In general, in the case of exercise alone, a user brightens up dull moments while watching a movie or broadcast program from a monitor positioned on the front of a fitness equipment. However, it is difficult to find out a movie or broadcast program that is suitable for the exercise time in every single time. Therefore, watching movie or broadcast program may not maintain an interest in exercise in a long term.

Exercise alone may be continued for a long period of time when it is done along with a partner. Treadmills or cycling equipment positioned in parallel could be used with the partner. In this case, the number of partners whom a person can exercise with conversation would be not more than two persons who are on the left and the right. Moreover, partner should arrive at an exercise place on time, and unoccupied fitness equipment set by side should be secured. Therefore, exercising with partner also has a limitation as a method to prevent from losing an interest in exercise.

Some implementations of the disclosed technology are illustrated in the drawings and are described in detail through the detailed description. It is however to be understood that the disclosed technology is not intended to be limited to the specific implementations and the disclosed technology includes all changes, equivalents and substitutions which fall within the spirit and technological scope of the disclosed technology.

Hereinafter, various implementations of the disclosed technology will be described in detail with reference to the accompanying drawings so that those skilled in the art can easily carry out the disclosed technology. In the following detailed description of the embodiments of the disclosed technology, a detailed description of known functions or configurations will be omitted. The same reference numerals are used throughout the drawings for portions having similar functions and actions. Furthermore, numbers (for example, the first and the second) used in the entire specification are merely identification symbols for distinguishing one element from the other element.

In addition, in the entire specification, when a part is referred to as being "connected" with another part, it is not only a case where it is directly connected, but also a case where it is indirectly connected with another element therebetween. Also, "comprising" and "including" mean that other components may be included, rather than excluding other components, unless specifically stated otherwise.

The term "unit" as used herein may include software, hardware, or a combination thereof depending on the context in which the term is used. For example, the software may be machine code, firmware, embedded code, application software, or a combination thereof. Also, for example, the hardware may be a circuit, a processor, a computer, an integrated circuit, integrated circuit cores, or a combination thereof. Two or more elements expressed as "unit" may be merged into a single element or one element may be divided into two or more elements for each subdivided function.

Hereinafter, various implementations of the disclosed technology will be described in detail with reference to the accompanying drawings so that those skilled in the art can easily carry out the disclosed technology.

Figure 1:
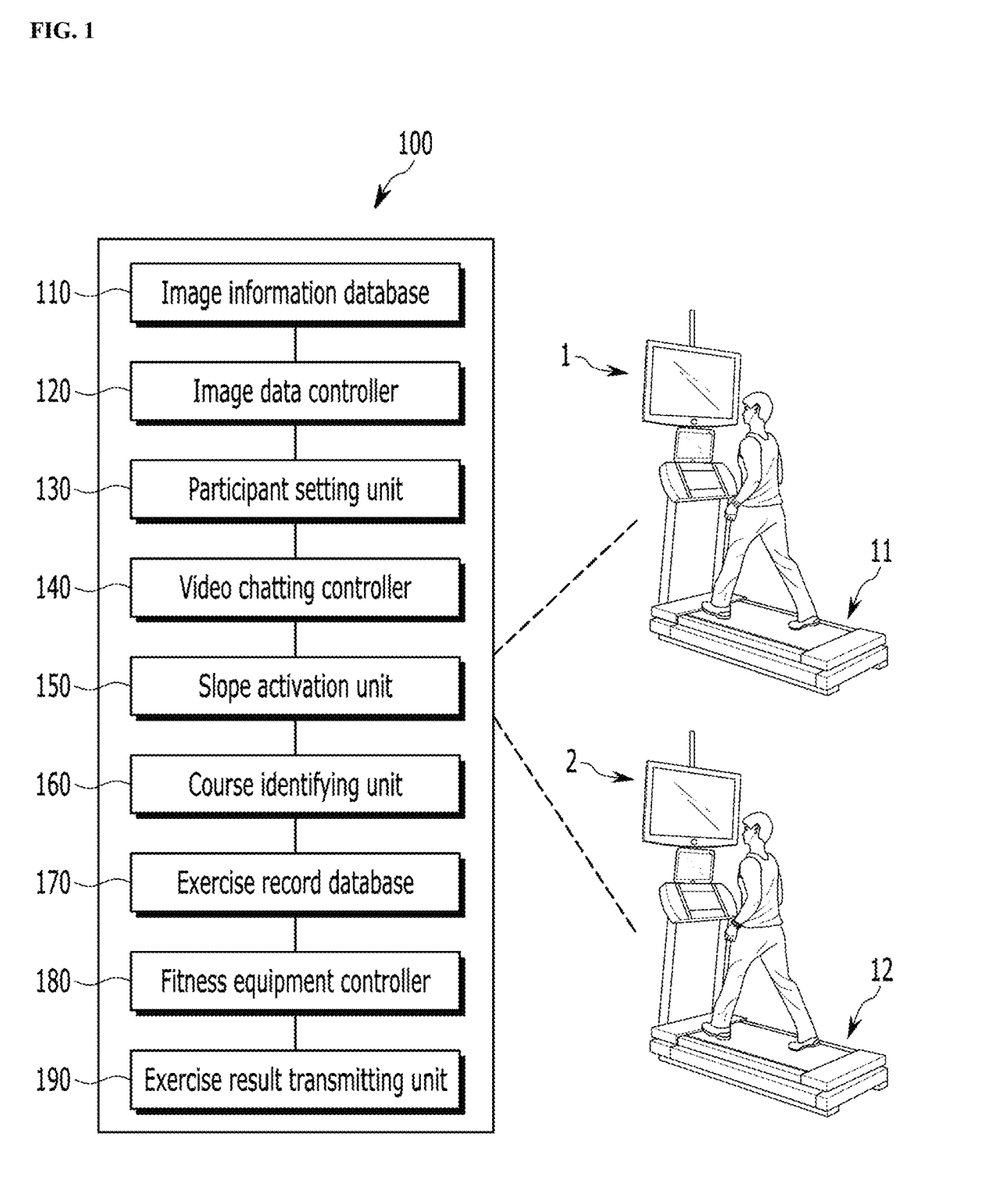
FIG. 1 is an exemplary diagram showing a schematic configuration of a system for providing a virtual exercise place according to an implementation of the disclosed technology.
Figure 2:
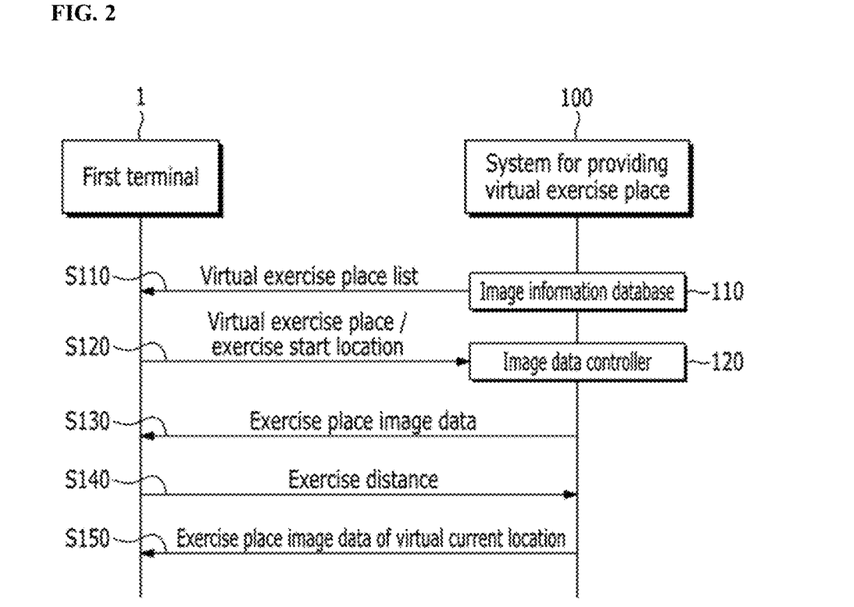
FIG. 2 is an exemplary flowchart showing a method of providing virtual exercise place in the system for providing a virtual exercise place according to an implementation of the disclosed technology.

FIG. 1 is an exemplary diagram showing a schematic configuration of a system for providing a virtual exercise place according to an implementation of the disclosed technology. FIG. 2 is an exemplary flowchart showing a method of providing virtual exercise place in the system for providing a virtual exercise place according to an implementation of the disclosed technology.

The system 100 for providing a virtual exercise place according to an implementation of the disclosed technology is connected to at least one terminal 1 or 2 and at least one fitness equipment 11 and 12 capable of calculating an exercise distance through a network and performs a function to transmit an image of a virtual exercise place to a terminal.

In this case, the network means connection architecture through which information can be exchanged between nodes, such as terminals, fitness equipment and servers. Examples of the network include a 3$^{rd}$ Generation Partnership Project (3GPP) network, a Long Term Evolution (LTE) network, a World Interoperability for Microwave Access (WIMAX) network, the Internet, a Local Area Network (LAN), a Wireless Local Area Network (Wireless LAN), a Wide Area Network (WAN), a Personal Area Network (PAN), a Bluetooth network, a satellite broadcasting network, an analog broadcasting network, and a Digital Multimedia Broadcasting (DMB) network, but are not limited thereto.

The terminal of a user may be implemented using a computer capable of accessing a server or terminal at a remote place over the network. In this case, the computer may include a notebook, desktop, laptop, etc. on which a web browser has been mounted, for example. Furthermore, the terminal of a user may be implemented using a terminal capable of accessing a server or terminal at a remote place over the network. The terminal of a user is a wireless communication device that guarantees portability and mobility, for example. The terminal may include all of kinds of handheld-based wireless communication devices, such as a Personal Communication System (PCS), a Global System for Mobile communications (GSM), Personal Digital Cellular (PDC), a Personal Handyphone System (PHS), a Personal Digital Assistant (PDA), International Mobile Telecommunication (IMT)-2000, Code Division Multiple Access (CDMA)-2000, W-Code Division Multiple Access (W-CDMA) and Wireless Broadband Internet (Wibro) terminals, a smartphone, a smartpad, and a tablet PC. The terminals 1 and 2 are installed on the front, side or upper part of the fitness equipment 11 and 12 and preferably include large-sized monitors capable of displaying an image. The terminals 1 and 2 may be connected to a large monitor installed in the fitness equipment 11 and 12 to transmit video and audio signals. Furthermore, the terminal preferably includes a camera and a microphone. The fitness equipment is fitness equipment, such as a treadmill or cycling equipment. Equipment using a method of calculating a moving distance based on exercise may be applied to the fitness equipment.

The system 100 for providing virtual exercise place may include an image information database 110, an image data controller 120, a participant setting unit 130, a video chatting controller 140, and a slope activation unit 150.

The image information database 110 is a data storage server, and location-based image data related to a virtual exercise place may be stored. For instance, the image data captured by a 360-degree camera in every coordinate value based on GPS coordinates may be stored, and everyplace in the world may become the virtual exercise place. Furthermore, the image information database 110 may include gradient data for each location of the location-based image data related to the virtual exercise place. For instance, the gradient data which are slopes measured in all directions of 360-degree based on GPS coordinates may be stored.

Figure 3:
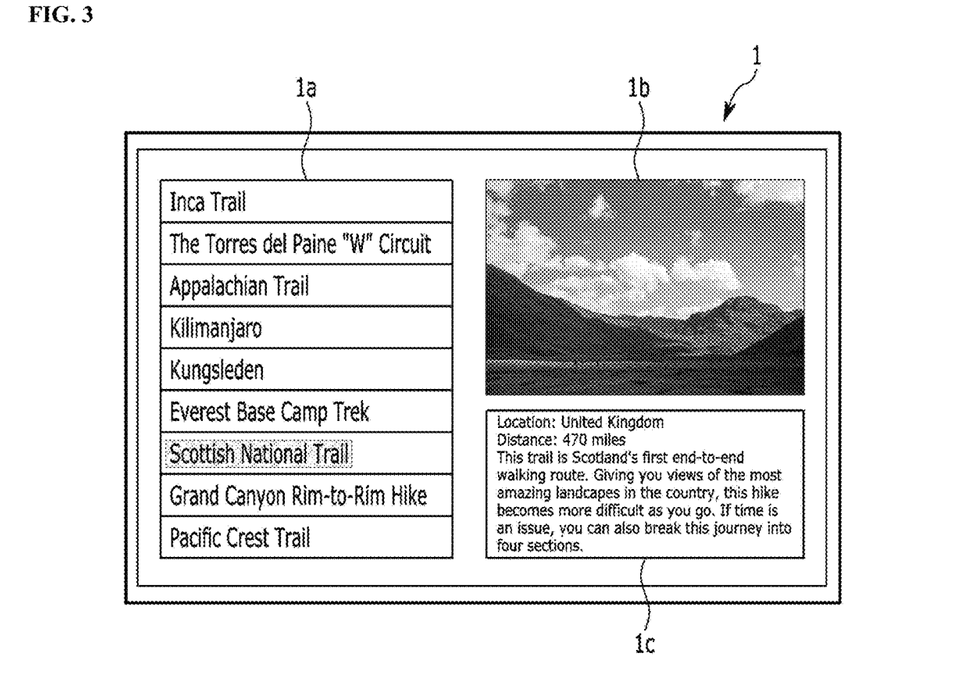
FIG. 3 is an exemplary diagram showing the virtual exercise place selection screen displayed on a terminal of the system for providing a virtual exercise place according to an implementation of the disclosed technology.
Figure 4:
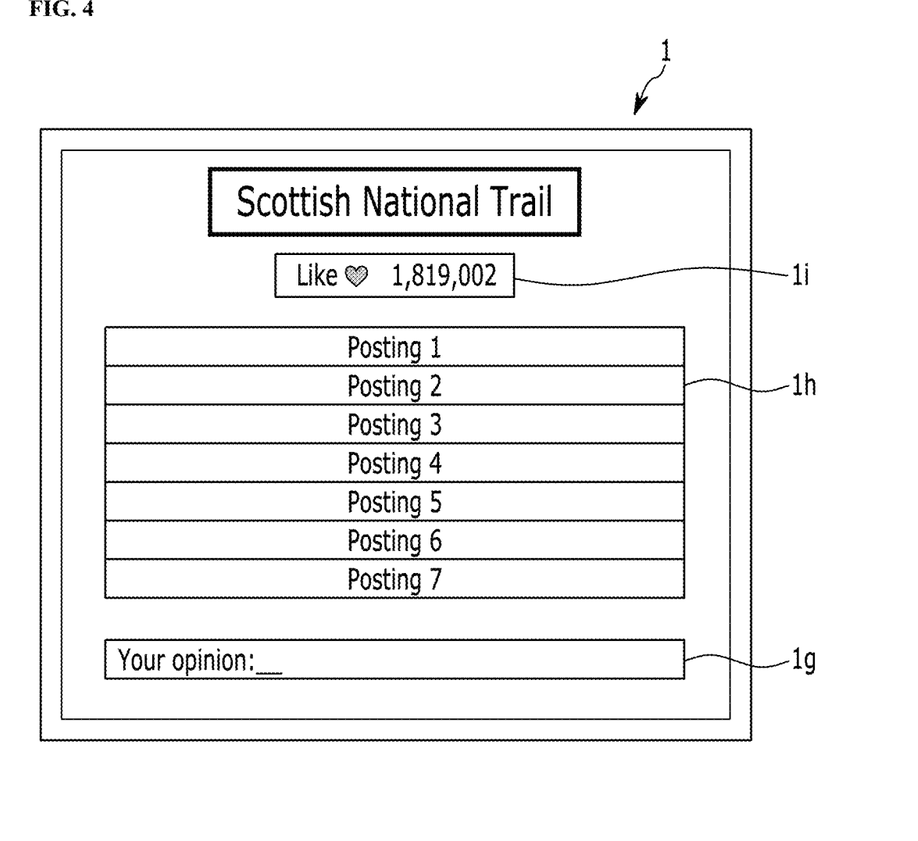
FIG. 4 is an exemplary diagram showing the virtual exercise place posting screen displayed on the terminal of the system for providing a virtual exercise place according to an implementation of the disclosed technology.
Figure 5:
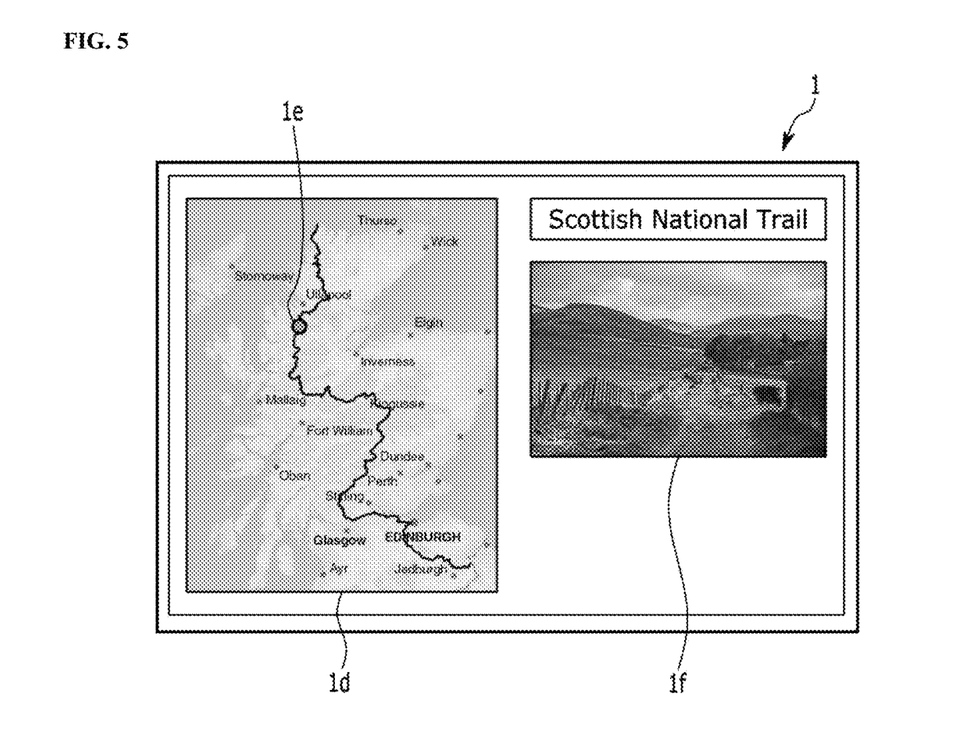
FIG. 5 is an exemplary diagram showing an exercise start location selection screen displayed on the terminal of the system for providing a virtual exercise place according to an implementation of the disclosed technology.

FIG. 3 is an exemplary diagram showing the virtual exercise place selection screen displayed on the terminal of the system for providing a virtual exercise place according to an implementation of the disclosed technology. FIG. 4 is an exemplary diagram showing the virtual exercise place posting screen displayed on the terminal of the system for providing a virtual exercise place according to an implementation of the disclosed technology. FIG. 5 is an exemplary diagram showing an exercise start location selection screen displayed on the terminal of the system for providing a virtual exercise place according to an implementation of the disclosed technology. The disclosed technology is not limited to the illustrated configuration.

A first user checks a virtual exercise place list 1a (S110) by accessing the image information database 110 through his or her own first terminal 1, and then may select the virtual exercise place where he or she wants to exercise. In order to help the selection of the first user, the first terminal 1 may receive and display a photo 1b and information 1c for the virtual exercise place that is written in the virtual exercise place list 1a from the image information database 110.

The virtual exercise place may include all of worldwide roads on which one may exercise. For instance, the virtual exercise place in Korea may include Cheonggye creek Night Walk, way to Mount Seorak Towangseong Falls, DMZ Punch Bowl Dulle-gil Trail (Meonmejjaegil), Namhansanseong Dulle-gil Trail 5th Course (Seonggwak-gil), etc.

The information 1c as to the virtual exercise place may include information (history, distance, difficulty, etc.) of the corresponding exercise place. In the information 1c as to the virtual exercise place, an input window 1g whereby an opinion of the user regarding the virtual exercise place may be posted may be set to be presented, and a list window 1h which shows the postings reflecting the opinion of the user. Furthermore, the user may express his or her preference of the virtual exercise place through preference input window 1i by pressing "like" or similar button, and may check the numbers of "like" that other users pressed. In this way, the first user may post his or her opinion regarding the virtual exercise place, or may read opinions that other users posted. Such postings may be shared on other SNS programs (for instance, Facebook, Instagram, KakaoStory, Pod cast, etc.), and contents and posting described in the information 1c as to the virtual exercise place may be shared together.

When the first user selects the virtual exercise place, a screen 1d on which an exercise start location can be selected is displayed on the first terminal 1. Exercisable courses in the virtual exercise place are displayed, and the user may select the exercise start location 1e. When the user selects the exercise start location 1e, a scenery if of the front view from the exercise start location 1e is illustrated. The scenery 1f may be adjusted depending on the exercise direction.

The image data controller 120 may receive from the first terminal 1 the virtual exercise place and the exercise start location (S120), select location-based image data related to the virtual exercise place (hereinafter "location-based image data related to the virtual exercise place" is referred to as "exercise place image data") from the image information database 110, and transmit them to the first terminal 1 (S130). For instance, the image data controller 120 may select the exercise place image data corresponding to the GPS coordinates of the virtual exercise place selected by the first user and transmit them to the first terminal 1, and the exercise place image data if may be displayed on the first terminal. In FIG. 5, the exercise place image data if has been displayed on a small-sized screen, but it may be shifted into a full screen mode.

The image data controller 120 may receive an exercise distance information calculated by the first fitness equipment 11 from the first terminal 1 connected to the first fitness equipment 11 (S140), and display on the first terminal 1 the exercise place image data corresponding to a location moved by an exercise distance from the exercise start location (hereinafter "location moved by the exercise distance from the exercise start location" is referred to as "virtual current location")(S150). For instance, the image data controller 120 may obtain the exercise distance information from the first terminal 1, in a wired/wireless method, connected to a publicly known distance calculator equipped in treadmill or cycling equipment, select from the image information database 110 the exercise place image data corresponding to GPS coordinates of the virtual current location where the exercise distance information is reflected, transmit them to the first terminal 1, and the exercise place image data if for the virtual current location may be displayed on the first terminal 1.

In this way, as the first user exercises on the first fitness equipment, the exercise place image data is continuously updated in real time, as if the first user enters and exercises in the virtual exercise place, the scenery displayed to the first user via the first terminal 1 is changed in accordance with the exercise distance.

The slope activation unit 150 may apply to the first fitness equipment 11 a load corresponding to gradient data corresponding to the virtual current location, or a slope corresponding to gradient data corresponding to the virtual current location, through the first terminal 1 that is connected to the load control device of the first fitness equipment 11 in a wired or wireless way. For instance, when a slope increases, it may increase the load of cycling equipment or the slope of a foothold of treadmill, thereby making exercise of the first user harder.

Figure 6:
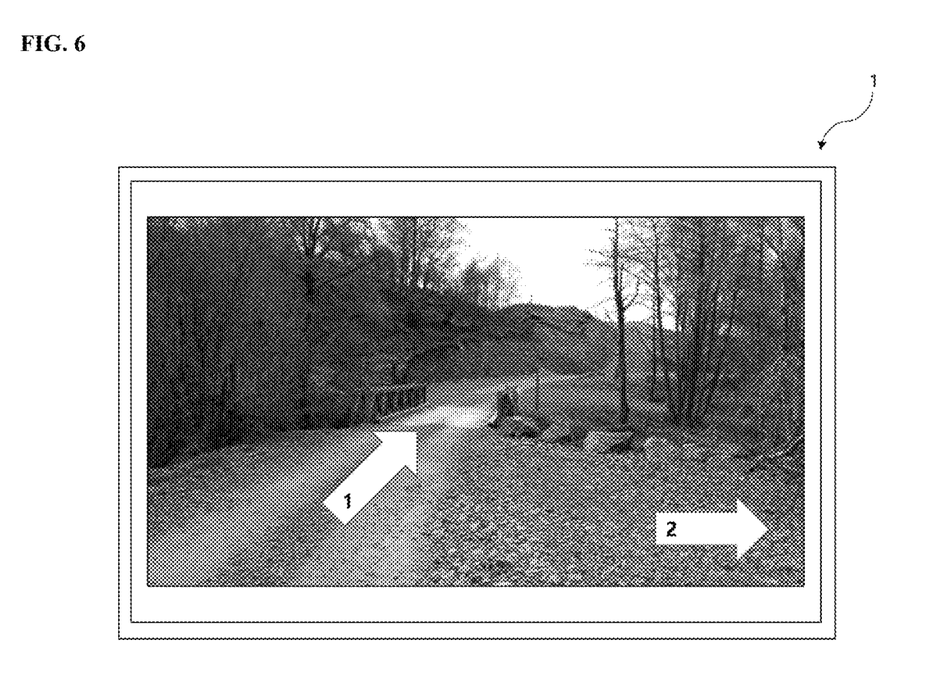
FIG. 6 is an exemplary diagram showing a course change screen displayed on the terminal of the system for providing a virtual exercise place according to an implementation of the disclosed technology.

FIG. 6 is an exemplary diagram showing a course change screen displayed on the terminal of the system for providing a virtual exercise place according to an implementation of the disclosed technology.

The system for providing a virtual exercise place according to an implementation of the disclosed technology may further comprise a course identifying unit 160.

While the first user is exercising along a course firstly determined by the first fitness equipment, the first user may change the course into a new course. When the virtual current location reaches a course selection point (e.g., a forked road) in the exercise place image data, the image data controller 120 transmits to the first terminal 1 the information that the course can be changed and a course selection message including selectable courses, and the first user may select a desired course (e.g., No. 1 arrow or No. 2 arrow in FIG. 6) through the first terminal 1. The exercise place image data corresponding to the selected course by the first terminal 1 may be displayed on the first terminal 1.

The camera equipped in the first terminal 1 shoots a movement of hand of the user in exercise, and after the course identifying unit 160 searches for an identical pattern to a pre-stored movement pattern from the movement of hand of the user, it may decide user-intended course according to the command given to the identical pattern. For instance, when the user swings the hand from left to right, the course identifying unit 160 finds a pattern of swinging the hand from left to right among the stored movement patterns, and if the meaning of that pattern is set to choose right direction of the course, the course identifying unit 160 decides that the right direction of the course has been chosen at the course selection point, and transmits it to the image data controller 120 in order to display the selected course.

Figure 7:
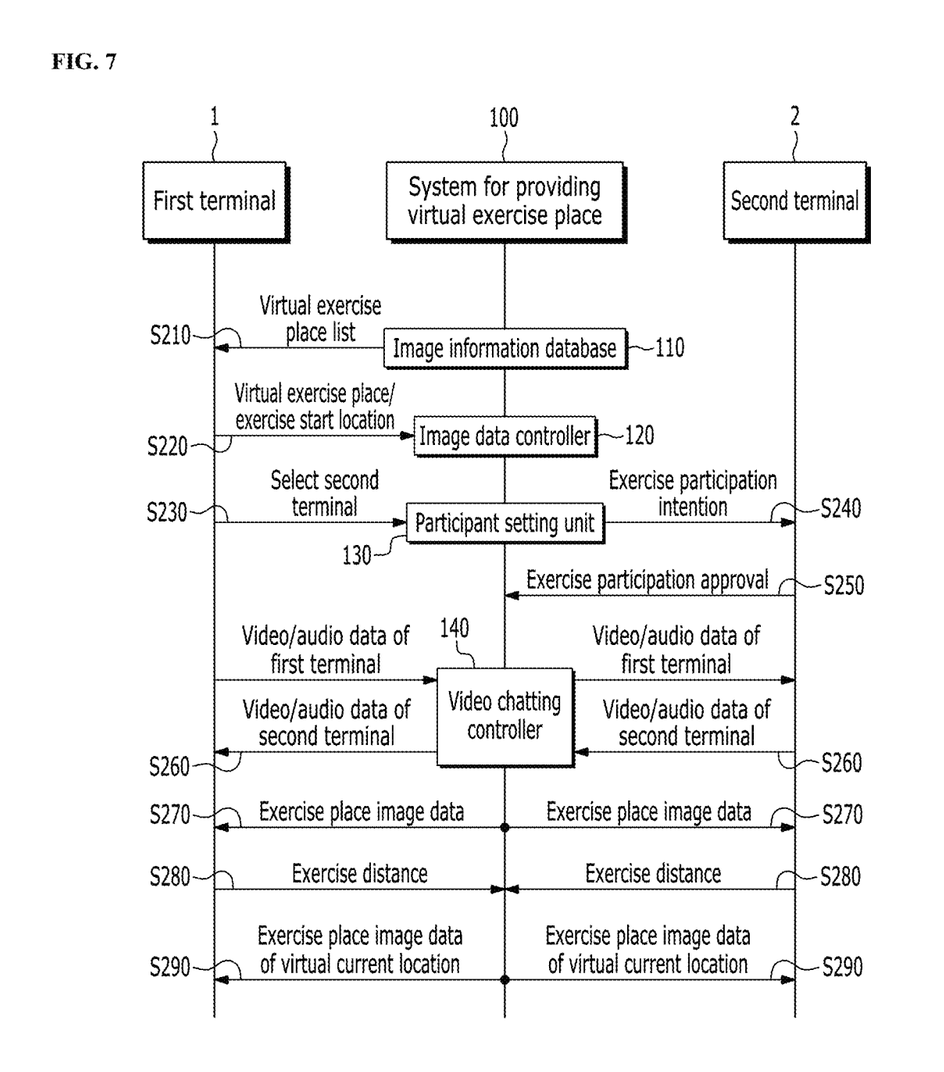
FIG. 7 is an exemplary flowchart showing a method of providing virtual exercise place applied when a multiple of the users use the system for providing a virtual exercise place according to an implementation of the disclosed technology.
Figure 8:
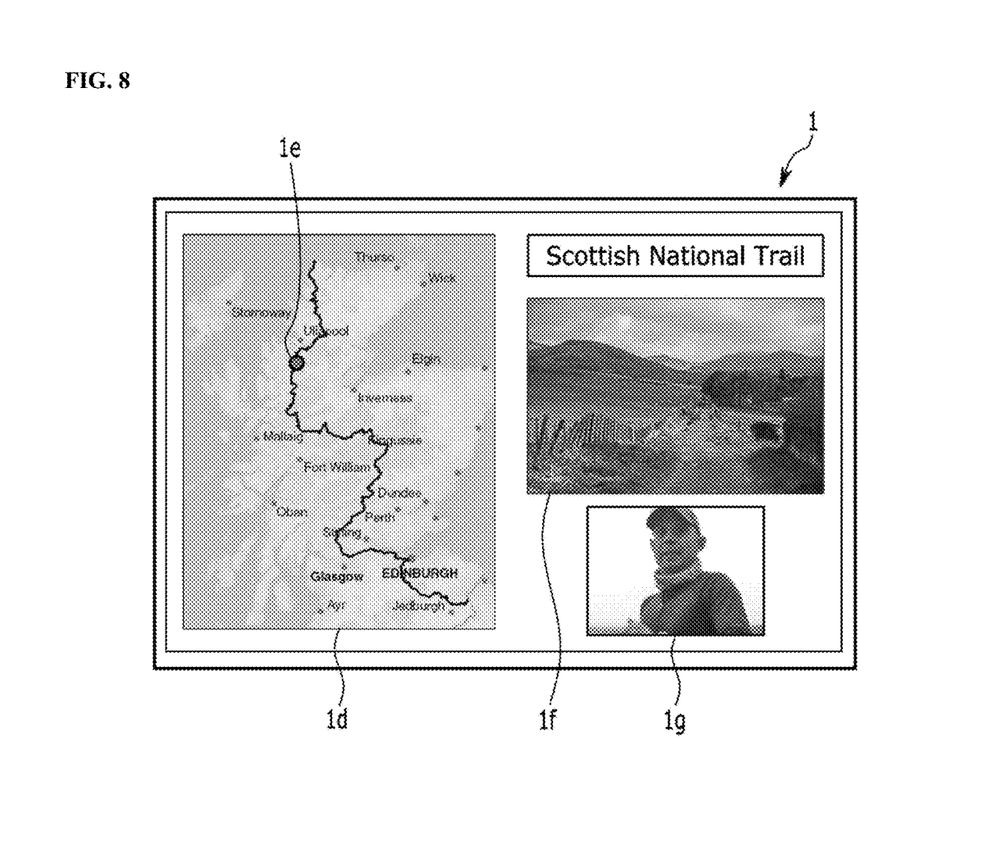
FIG. 8 is an exemplary diagram showing the exercise start location selection screen displayed on the terminal when a multiple of the users use the system for providing a virtual exercise place according to an implementation of the disclosed technology.

FIG. 7 is an exemplary flowchart showing a method of providing virtual exercise place applied when a multiple of users use the system for providing a virtual exercise place according to an implementation of the disclosed technology. FIG. 8 is an exemplary diagram showing an exercise start location selection screen displayed on the terminal when a multiple of users use the system for providing a virtual exercise place according to an implementation of the disclosed technology.

The first user checks the virtual exercise place list 1a (S210) by accessing the image information database 110 through his or her first terminal 1, and then may select the virtual exercise place where he or she wants to exercise. As illustrated in FIG. 3, in order to help the selection of the first user, the first terminal 1 may receive and display a photo 1b and information 1c of the virtual exercise place that is written in the virtual exercise place list 1a from the image information database 110.

The virtual exercise place may include all of worldwide roads on which exercise can be taken. For instance, the virtual exercise place in Korea may include Cheonggye creek Night Walk, way to Mount Seorak Towangseong Falls, DMZ Punch Bowl Dulle-gil Trail (Meonmejjaegil), Namhansanseong Dulle-gil Trail 5th Course (Seonggwak-gil), etc.

The information 1c as to the virtual exercise place may include information (history, distance, difficulty, etc.) of the corresponding exercise place. In the information 1c as to the virtual exercise place, an input window 1g which an opinion of the user regarding the virtual exercise place may be posted may be set to be presented, and a list window 1h which shows the postings where the opinions of the users are reflected. Furthermore, the user may express his or her preference of the virtual exercise place through preference input window 1i by pressing "like" button, and may check the numbers of "like" that other users pressed. In this way, the first user may post his or her opinion regarding the virtual exercise place, or may read opinions that other users posted. Such postings may be shared on other SNS programs (for instance, Facebook, Instagram, KakaoStory, Pod cast, etc.), and contents and posting described in the information 1c about the virtual exercise place may be shared together.

When the first user selects the virtual exercise place, as illustrated in FIG. 5, a screen 1d on which the exercise start location can be selected, is displayed on the first terminal 1. Exercisable courses in the virtual exercise place are displayed, and the user may select the exercise start location 1e (S220). When the user selects the exercise start location 1e, a scenery if of the front view from the exercise start location 1e is illustrated.

The first user may select one or more partners to exercise together in the virtual exercise place. The first user may select the second user as an partner to exercise together through the first terminal 1, and the first terminal 1 transmits to the participant setting unit 130 a signal notifying that the second user is selected as an exercise partner (S230). The second user may be a person who lives in a different country, or who exercises in the same space. The participant setting unit 130 may transmit to the first terminal 1 the list of accessing users in the system for providing virtual exercise place, and the first user can easily select a partner for exercise.

A signal asking an exercise participation intention may be transmitted by the participant setting unit 130 to the second terminal 2 of the second user (S240), and the second user may transmit through the second terminal 2 to the participant setting unit 130 a joint exercise start signal to accept the exercise participation (S250), or may transmit a joint exercise refusal signal to decline the exercise participation. When the participant setting unit 130 receives the joint exercise start signal from the second terminal 2, an appearance 1g of the second user photographed by the second terminal 2 is displayed on the first terminal 1.

In FIGS. 1 and 7, the system 100 for providing virtual exercise place is illustrated as being connected to two terminals 1 and 2, however this is only an example for convenience of description of the disclosed technology, of course, it is possible that three or more terminals are connected to the system 100 for providing virtual exercise place. Accordingly, the system 100 for providing virtual exercise place may be used in a group exercise of a group such as a club, and the method that celebrities, who accept to participate in exercise, among the celebrities of internal and external sports, medicine, entertainment, politics, culture and art fields, participate in exercise along with multiple users may be used. Moreover, the participant setting unit 130 may include a virtual character (famous comic character, character having an image of the user or celebrity, a virtual trainer character, etc.) to the exercise partner list and may provide them to the first terminal 1. Such methods may greatly enhance users' interest and a degree of participation. The video chatting controller 140 receives from the first terminal 1 the video data including the appearance of the first user photographed by the camera of the first terminal 1 and the audio data including the voice of the first user recorded by the microphone of the first terminal 1, and may receive from the second terminal 2 the video data including the appearance of the second user photographed by the camera of the second terminal 2 and the audio data including the voice of the second user recorded by the microphone of the second terminal 2. The video chatting controller 140 transmits the video data and the audio data of the first user to the second terminal 2, and may transmit the video data and the audio data of the second user to the first terminal 1 (S260).

If a virtual character is selected as an exercise partner, the video chatting controller 140 may transmit the video data and the audio data of the selected character to the first terminal 1. In this case, it is possible that the virtual character may communicate and conduct by artificial intelligence. It is preferable that the virtual character runs at the same speed as the first user.

Moreover, the video chatting controller 140 transmits background music (song, pop song, classics, etc.) to the terminals 1 and 2 so that exercise can be done with background music.

After the image data controller 120 receives the virtual exercise place and the exercise start location from the first terminal 1, it may select the exercise place image data from the image information database 110 and transmit them to the first terminal 1 and the second terminal 2 (S270). For instance, the image data controller 120 selects the exercise place image data corresponding to the GPS coordinates of the virtual exercise place selected by the first user and may transmit them to the first terminal 1 and the second terminal 2, and the exercise place image data 1f may be displayed on the first terminal 1 and the second terminal 2. In FIG. 8, the exercise place image data if and the second user 1g are displayed on a small-sized screen, but it is possible to switch the desired screen among them to the mode displayed on the entire screen.

The image data controller 120 receives the exercise distance information calculated by the first fitness equipment 11 (S280), and may display the exercise place image data corresponding to the virtual current location on the first terminal 1 and the second terminal 2 (S290). For instance, the image data controller 120 may obtain the exercise distance information from the first terminal 1 and the second terminal 2 which is, in a wired/wireless method, connected to the publicly-known distance calculator equipped in the treadmill or the cycling equipment, select in the image information database 110 the exercise place image data corresponding to the GPS coordinates of the virtual current location where the exercise distance information is reflected and transmit them to the first terminal 1 and the second terminal 2, and the exercise place image data if related to the virtual current location may be displayed on the first terminal 1 and the second terminal 2.

In this way, as the first user and the second user exercise with the first fitness equipment and the second fitness equipment, respectively, the exercise place image data continuously change, and as if the first user and the second user enter the virtual exercise place and exercise together, the scenery shown to the first user and the second user via the first terminal 1 and the second terminal 2 may change in accordance with the exercise distance.

It is possible that a difference between the virtual current location of the first user and the virtual current location of the second user may be generated due to a difference in the exercise speed between the first user and the second user, and in this case, different exercise place image data may be displayed on the first terminal 1 and the second terminal 2, respectively.

The slope activation unit 150, through the first terminal 1 and the second terminal 2 that are connected in a wired or wireless method to the load control device of the first fitness equipment 11 and the second fitness equipment 12, may apply a load corresponding to gradient data corresponding to the virtual current location to the first fitness equipment 11 and the second fitness equipment 12, or apply a slope corresponding to gradient data corresponding to the virtual current location to the first fitness equipment 11 and the second fitness equipment 12. For instance, when a slope increases, by increasing a load (rotating resistance) of cycling equipment, or by increasing a slope of treadmill's foothold in order to make the exercise of the first user and the second user harder.

Meanwhile, while the first user and the second user exercise along the course firstly determined by the first terminal 1, they may change it into a new course. When the virtual current location reaches the course selection point (e.g., a forked road) in the exercise place image data, the image data controller 120 transmits the first terminal 1 and/or the second terminal 2 the information that the course can be changed and the course selection message including selectable courses, and any one of the first user and the second user may select the desired course (e.g., No. 1 arrow or No. 2 arrow in FIG. 6) through the first terminal 1 or the second terminal 2. The exercise place image data corresponding to the firstly selected course by any one of the first terminal 1 and the second terminal 2 may be displayed on the first terminal 1 and the second terminal 2, and thus the user who first arrives the forked road may have the priority right to decide the course, whereby it has an effect to enhance an interest in exercise through a competition.

In addition, when the virtual current location of another user who accesses the system 100 and exercises reaches the virtual current location of the first user or the second user, the video chatting controller 140 displays an appearance of said another user on the first terminal 1 and the second terminal 2 and outputs a voice to the first terminal 1 and the second terminal 2, and notifies that said another user exercises in the place where the first user and the second user exercise, whereby it may enhance interactions among users and give users an excitement of the virtual moving exercise so that they are further immersed in the virtual exercise place. Like this, the users who have met in the virtual exercise space can transmit a joint signal to the participant setting unit 130 and move together. In this case, the same exercise place image data will be displayed on the terminals of the users.

In detail, when the virtual current location of a third terminal, which the first terminal 1 has not asked to participate in the exercise, approaches the virtual current location of the first terminal 1 or the second terminal 2, the video chatting controller 140 may receive from the third terminal the video data of the third user using the third terminal, photographed by the camera of the third terminal, and the audio data including voice of the third user, recorded by the microphone of the third terminal, transmit the video data and the audio data of the third user to the first terminal and the second terminal, and transmit the video data and the audio data of the first user and the second user to the third terminal. Moreover, the participant setting unit 130 may transmit the information (e.g., name, photo, gender, etc.) of the third user to the first terminal 1 and the second terminal 2, and transmit the information (e.g., name, photo, gender, etc.) of the first user and the second user to the third terminal vice versa.

The first user or the second user, through the first terminal 1 or the second terminal 2, may select the third user as an exercise partner, and in order for this, the first terminal 1 or the second terminal 2 may transmit a signal notifying that the third user has been selected as the exercise partner to the participant setting unit 130.

A signal for asking the exercise participate intention may be transmitted by the participant setting unit 130 to the third terminal of the third user, and the third user may transmit through the third terminal to the participant setting unit 130 a joint exercise start signal to accept an exercise participation, or a joint exercise refusal signal to decline the exercise participation. When the participant setting unit 130 receives the joint exercise start signal from the third terminal, the appearance of the third user photographed by the third terminal may be displayed on the first terminal 1 and the second terminal 2.

Meanwhile, the third user may select the first user and the second user as exercise partners through the third terminal, and for this purpose, the third terminal may transmit a signal notifying that the first user and the second user have been selected as the exercise partners to the participant setting unit 130.

A signal for asking the exercise participation intention may be transmitted by the participant setting unit 130 to the first terminal 1 and the second terminal 2 of the first user and the second user, and the first user or the second user may transmit through the first terminal 1 or the second terminal 2 to the participant setting unit 130 a joint exercise start signal to accept an exercise participation, or a joint exercise refusal signal to decline the exercise participation. When the participant setting unit 130 receives the joint exercise start signal from the first terminal 1 or the second terminal 2, the appearance of the first user and the second user photographed by the first terminal 1 and the second terminal 2 may be displayed on the third terminal.

In such a way, when the first user, the second user, and the third user exercise together, the same exercise place image data may be displayed on the first terminal 1, the second terminal 2, and the third terminal 3.

The system 100 for providing virtual exercise place may provide an event to the users who exercise together. The image data controller 120 provides the user who exercise together with a first-come first-served basis event of a particular section (it may be the course out of the original course), and the users may select the path for themselves at every forked road and sprint at full speed in order to arrive at the virtual target point first. When this event begins, the exercise place image data may be displayed separately and differently on the users' terminals, and the participant setting unit 130 may reward to the first arrival user at the virtual target point, such as extending using period of the system 100 for providing virtual exercise place. When all the users arrive at the virtual target point, the image data controller 120 may transmit the same exercise place image data to the terminals of the users like in the beginning so that the users can exercise together again.

Figure 9:
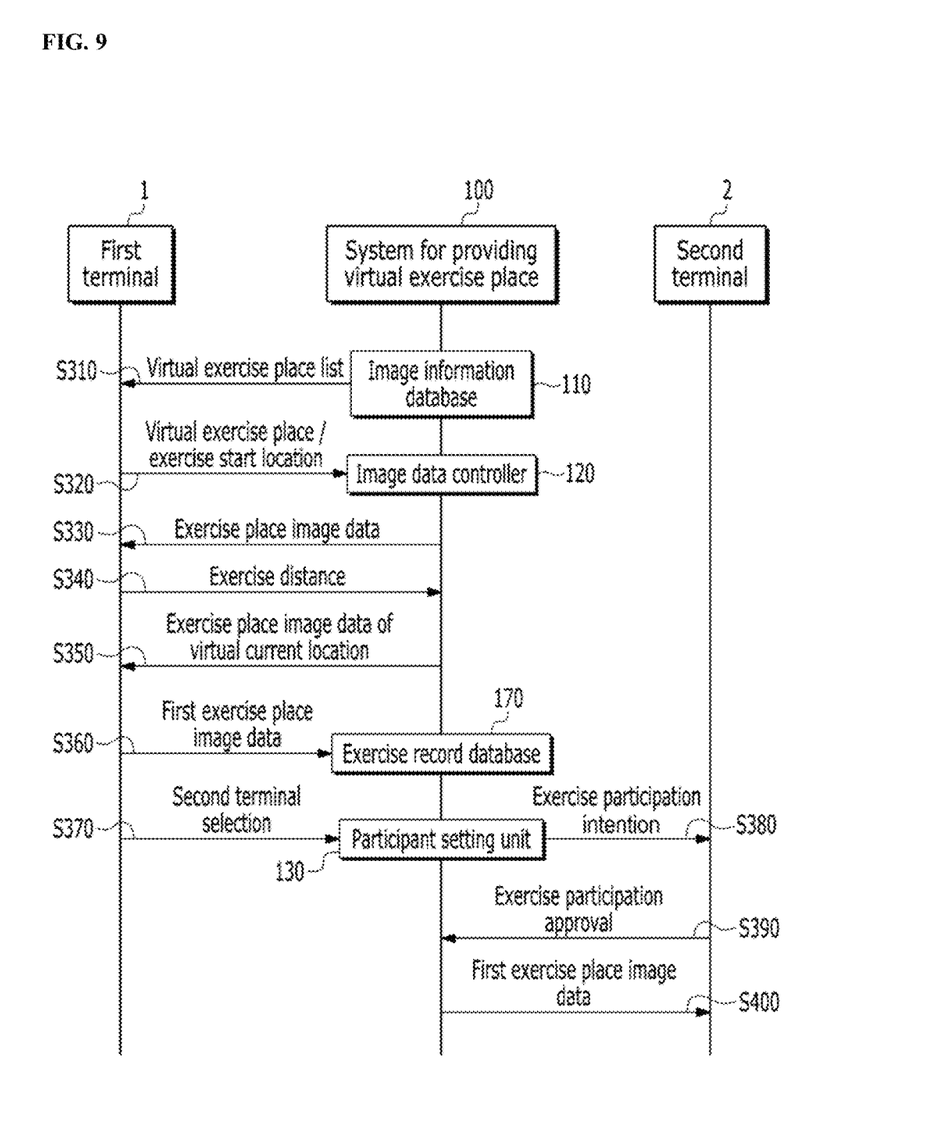
FIG. 9 is an exemplary flowchart showing a method of providing virtual exercise place applied when a multiple of the users use the system for providing a virtual exercise place according to an implementation of the disclosed technology at a different time.

FIG. 9 is an exemplary flowchart showing a method of providing virtual exercise place applied when a multiple of users use the system for providing a virtual exercise place according to an implementation of the disclosed technology at a different time.

A system for providing a virtual exercise place according to an implementation of the disclosed technology may further include an exercise record database 170, a fitness equipment controller 180, and an exercise result transmitting unit 190.

The exercise record database 170 may be used in a situation where the first user and the second user cannot exercise at the same time. For instance, the circumstance where the first user lives in Korea, and the second user lives in the U.S. would be the example.

The first user checks the virtual exercise place list 1a by accessing the image information database 110 through his or her own first terminal 1 (S310), and then may select the virtual exercise place where he or she wants to exercise. In order to help the selection of the first user, the first terminal 1 may receive and display the photo 1b and the information 1c for the virtual exercise place that is written in the virtual exercise place list 1a from the image information database 110.

When the first user selects the virtual exercise place, the screen 1d on which an exercise start location can be selected is displayed on the first terminal 1. Excisable courses in the virtual exercise place are displayed, and the user may select the exercise start location 1e. When the user selects the exercise start location 1e, the scenery if of the front view from the exercise start location 1e is illustrated. The scenery if may be adjusted depending on the exercise direction.

The image data controller 120 may receive from the first terminal 1 the virtual exercise place and the exercise start location (S320), select the exercise place image data from the image information database 110, and transmit them to the first terminal 1 (S330). For instance, the image data controller 120 may select the exercise place image data corresponding to the GPS coordinates of the virtual exercise place selected by the first user and transmit them to the first terminal 1, and the exercise place image data if may be displayed on the first terminal.

The image data controller 120 may receive the exercise distance information calculated by the first fitness equipment 11 from the first terminal 1 connected to the first fitness equipment 11 (S340), and display on the first terminal 1 the exercise place image data corresponding to the virtual current location (S350). For instance, the image data controller 120 may obtain the exercise distance information from the first terminal 1, in a wired/wireless method, connected to a publicly known distance calculator equipped in treadmill or cycling equipment, select from the image information database 110 the exercise place image data corresponding to GPS coordinates of the virtual current location where the exercise distance information is reflected, transmit them to the first terminal 1, and the exercise place image data if for the virtual current location may be displayed on the first terminal 1.

As the first user exercises on the first fitness equipment, the exercise place image data is continuously updated in real time, as if the first user enters and exercises in the virtual exercise place, the scenery displayed to the first user via the first terminal 1 is changed in accordance with the exercise distance.

The exercise place image data from the exercise start location to the virtual current location, displayed on the first terminal 1 (hereinafter "exercise place image data from the exercise start location to the virtual current location, displayed on the first terminal" is referred to as "first exercise place image data") may be stored in the exercise record database 170 (S360). The first exercise place image data may include the video data of the first user using the first fitness equipment, photographed by the camera of the first terminal 1, and the audio data including the voice of the first user, recorded by the microphone of the first terminal 1.

The first user may select more than one user whom he or she wants to provide with the first exercise place image data. The first user may select the second user as a user whom the first user wants to provide with the first exercise place image data, through the first terminal 1, and the first terminal 1 may transmit to the participant setting unit 130 a signal notifying that the second user has been selected as a user whom the first user wants to provide with the first exercise place image data (S370). The participant setting unit 130 may transmit a signal for asking the exercise participation intention to the second terminal 2 of the second user (S380).

The second user who begins an exercise at the time different from the time when the first user exercised may transmit through the second terminal 2 to the participant setting unit 130 the joint exercise start signal to accept the exercise participation (S390), or the joint exercise refusal signal to decline the exercise participation. When the participant setting unit 130 receives the joint exercise start signal from the second terminal 2, the image data controller 120 may display the first exercise place image data stored in the exercise record database 170 on the second terminal 2 (S400).

The image data controller 120 may receive the exercise distance information calculated by the second fitness equipment and display the first exercise place image data corresponding to the virtual current location of the first exercise place image data corresponding to the virtual current location calculated by the second fitness equipment.

The fitness equipment controller 180 may control the speed of the second fitness equipment. The fitness equipment controller 180 may change the speed of the second fitness equipment in accordance with the speed at which the virtual current location of the first exercise place image data changes. In other words, the exercise speed of the second fitness equipment operates in accordance with the speed at which the first user exercised. Hence, the second user exercises with the first user's exercise intensity, and as the video data and the audio data of the first user are played, the second user would more clearly feel that the second user exercises with the first user.

The exercise result transmitting unit 190 may display on the second terminal a complex video data combining the first exercise place image data with the video data of the second user using the second fitness equipment, photographed by the camera of the second terminal 2 and/or the audio data including the voice of the second user using the second fitness equipment, recorded by the microphone of the second terminal 2 and store the complex video data displayed on the second terminal in the exercise record database 170, and then transmit them to the member account of the first user.

When the virtual current location of another user who accesses the system 100 for providing virtual exercise place and exercises reaches the virtual current location of the second user, The video chatting controller 140 displays an appearance of another user on the second terminal 2 and outputs a voice to the second terminal 2, and notifies that other users exercise in the place where the second user exercise, whereby it may enhance interactions among users and give users an excitement of the virtual moving exercise so that they are further immersed in the virtual exercise place.

In detail, when the virtual current location of the third terminal of the third user approaches the virtual current location of the second terminal 2, the video chatting controller 140 may receive from the third terminal the video data of the third user using the third terminal, photographed by the camera of the third terminal, and the audio data including the voice of the third user, recorded by the microphone of the third terminal, transmit the video data and the audio data of the third user to the second terminal, and transmit the video data and the audio data of the second user to the third terminal. Moreover, the participant setting unit 130 may transmit the information (e.g., name, photo, gender, etc.) of the third user to the second terminal, and transmit the information (e.g., name, photo, gender, etc.) of the second user to the third terminal vice versa.

The second user, through the second terminal 2, may select the third user as an exercise partner, and in order for this, the second terminal 2 may transmit a signal notifying that the third user has been selected as the exercise partner to the participant setting unit 130.

The signal for asking the exercise participation intention may be transmitted to the third terminal of the third user by the participant setting unit 130, and the third user may transmit through the third terminal to the participant setting unit 130 the joint exercise start signal to accept the exercise participation, or the joint exercise refusal signal to decline the exercise participation. When the participant setting unit 130 receives the joint exercise start signal from the third terminal, the appearance of the third user photographed by the third terminal may be displayed on the second terminal 2.

Meanwhile, the third user may select the second user as an exercise partner through the third terminal, and in order for this, the third terminal may transmit a signal notifying that the second user has been selected as the exercise partner to the participant setting unit 130.

The signal for asking the exercise participation intention may be transmitted to the second terminal 2 of the second user by the participant setting unit 130, and the second user may transmit through the second terminal 2 to the participant setting unit 130 the joint exercise start signal to accept the exercise participation, or the joint exercise refusal signal to decline the exercise participation. When the participant setting unit 130 receives the joint exercise start signal from the second terminal 2, the appearance of the second user photographed by the second terminal 2 may be displayed on the third terminal.

In such a way, when the second user and the third user exercise together, the same exercise place image data may be displayed on the third terminal 3.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve described results. Moreover, the separation of various system components in the embodiments described in this patent document should not be understood as requiring such separation in all embodiments. Only a few implementations and examples are described. Other implementations, enhancements and variations can be made based on what is described and illustrated in this patent document.

DESCRIPTION OF REFERENCE NUMERALS

110: image information database
120: image data controller
130: participant setting unit
140: video chatting controller
150: slope activation unit
160: course identifying unit
170: exercise record database
180: fitness equipment controller
190: exercise result transmitting unit

The invention claimed is:

1. A system for providing a virtual exercise place, the system being connected to a plurality of terminals and fitness equipment, each of said plurality of terminals comprising a video capturing device and an audio capturing device, the system comprising:
   an image information database in which location-based image data is stored, the location-based image data including exercise place image data relating to the virtual exercise place, the exercise place image data relating to the virtual exercise place including exercise location image data corresponding to each of a plurality of locations within the virtual exercise place;
   an image data controller configured to: (a) select from the image information database the exercise place image data relating to the virtual exercise place; (b) transmit to a first terminal the exercise location image data corresponding to an exercise start location received from the first terminal; (c) receive exercise distance information calculated by a first fitness equipment; and (d) display on the first terminal the exercise location image data corresponding to a virtual current location, the virtual current location corresponding to a location that is an exercise distance away from the exercise start location;
   an exercise record database configured to store the exercise location image data corresponding to the exercise start location and the exercise location image data corresponding to the virtual current location displayed on the first terminal;
   wherein, when a joint exercise start signal is transmitted from a second terminal to the image data controller, the image data controller displays on the second terminal the exercise location image data corresponding to the virtual current location.

2. The system of claim 1, further comprising a slope activation unit for controlling a resistance of the first fitness equipment based on gradient data.

3. The system of claim 2, further comprising a fitness equipment controller which controls a speed of the second fitness equipment;
   wherein, the fitness equipment controller changes the speed of the second fitness equipment based on data obtained from the first fitness equipment.

4. The system of claim 1, wherein:
   the first terminal comprises a camera and a microphone,
   and wherein the exercise location image data comprises corresponding to the virtual current location includes video data of the first user using the first fitness equipment, captured by the camera of the first terminal, and audio data including voice of the first user, recorded by the microphone of the first terminal.

5. The system of claim 1, wherein:
   the second terminal comprises a camera and a microphone;
   and wherein the exercise location image data corresponding to the virtual current location includes video data of the second user using the second fitness equipment, captured by the camera of the second terminal, and audio data including voice of the second user, recorded by the microphone of the second terminal.

6. The system of claim 1, further comprising a course identifying unit configured to make a course selection based on a hand gesture made by a first user.

* * * * *